(12) United States Patent
Roso et al.

(10) Patent No.: US 8,190,254 B2
(45) Date of Patent: May 29, 2012

(54) DEFIBRILLATOR

(75) Inventors: Bruno Roso, Bad Dürrheim (DE); Gero v. Wagner, Rottweil (DE)

(73) Assignee: Metrax GmbH, Rottweil (DE)

( * ) Notice: Subject to any disclaimer, the term of this patent is extended or adjusted under 35 U.S.C. 154(b) by 457 days.

(21) Appl. No.: 12/311,588

(22) PCT Filed: Dec. 7, 2007

(86) PCT No.: PCT/EP2007/010638
§ 371 (c)(1),
(2), (4) Date: Apr. 3, 2009

(87) PCT Pub. No.: WO2008/068028
PCT Pub. Date: Jun. 12, 2008

(65) Prior Publication Data
US 2010/0023077 A1    Jan. 28, 2010

(30) Foreign Application Priority Data
Dec. 7, 2006    (DE) .................... 20 2006 018 672 U

(51) Int. Cl.
*A61N 1/39*    (2006.01)
(52) U.S. Cl. .............. 607/5; 607/4; 607/6; 607/7; 607/8
(58) Field of Classification Search .................... 607/4–8
See application file for complete search history.

(56) References Cited

U.S. PATENT DOCUMENTS

| 5,243,975 A * | 9/1993 | Alferness et al. ............. 607/7 |
| 5,372,606 A | 12/1994 | Lang et al. |
| 5,591,211 A * | 1/1997 | Meltzer ............. 607/5 |
| 6,493,580 B1 | 12/2002 | Cansell et al. |
| 7,917,209 B2 * | 3/2011 | Joo et al. ............. 607/6 |
| 2003/0004547 A1 | 1/2003 | Owen et al. |

FOREIGN PATENT DOCUMENTS

| DE | 197 51 024 A1 | 5/1999 |
| DE | 100 15 152 A1 | 11/2000 |
| DE | 100 28 410 A1 | 2/2001 |
| DE | 102 54 481 B3 | 11/2002 |
| WO | WO 01/26732 A1 | 4/2001 |
| WO | WO 03/009895 A1 | 2/2003 |

* cited by examiner

*Primary Examiner* — Niketa Patel
*Assistant Examiner* — Joseph Stoklosa
(74) *Attorney, Agent, or Firm* — Pauley Petersen & Erickson

(57) ABSTRACT

A defibrillator for external application to a patient. The defibrillator includes a power storage unit for supplying a defibrillation shock. The power storage unit has a capacitor unit encompassing at least one capacitor. In order to adjust a defibrillation treatment to different patients, the defibrillator advantageously comprises several different capacitor units which have a capacity adapted to various patient impedances and are or can be coupled in a replaceable manner to the defibrillator.

18 Claims, 3 Drawing Sheets

DEFIBRILLATOR

BACKGROUND OF THE INVENTION

1. Field of the Invention

This invention relates to a defibrillator for external application to a patient, which has an energy storage unit for administering a defibrillation shock, which has a capacitor unit equipped with at least one capacitor.

2. Discussion of Related Art

A defibrillator is known from German Patent Reference DE 100 15 152 A1. An energy storage unit, which is built into the defibrillator for a defibrillation pulse to be administered to a patient, has a plurality of capacitors integrated into the unit and can be electrically connected to one another in series or parallel, in different ways, via controlled switches in order to produce the defibrillation energy. This makes it possible to adapt to different impedances of patients. This design requires a relatively complex control technique.

A similar design is taught by U.S. Patent Application Publication 2003/0004547 A1, in which five capacitors are connected both in series and in parallel in various configurations for the discharging procedure.

The adaptation of the defibrillation shock to the patient impedance is taught by various publications, such as U.S. Pat. No. 6,493,580, with an adaptation of the pulse duration to the patient impedance and with a cyclical BTE pulse (biphasic truncated exponential) taught by U.S. Pat. No. 5,372,606 with variation of the pulse length as a function of the patient impedance and taught by German Patent Reference DE 102 54 481 B3 with a current-controlled end stage.

If a plurality of capacitors are used as energy storage units, then in most cases, this facilitates the energy production through parallel connection of the capacitors. They are then connected in series for administration of the shock.

German Patent Reference DE 197 51 024 A1 discloses a defibrillator with a permanently built-in capacitor unit and accessories that are attachable, but that do not relate to the actual defibrillator electronics of the main device. The same is also true for the defibrillator disclosed in German Patent Reference DE 100 28 410 A1.

SUMMARY OF THE INVENTION

One object of this invention is to provide an external defibrillator that is better adapted to the properties of a patient.

This object is attained with the characteristics described in this specification and in the claims. In this case, a plurality of different capacitor units with capacitances matched to various patient impedances are provided, which are or can be interchangeably coupled to the defibrillator. This provides an adaptation of the capacitance of the energy storage unit in the form of a capacitor unit of an external defibrillator to the individual impedance of a patient in order to achieve particular characteristic values, such as amperage and current path during a defibrillation shock. The capacitor units are formed as modules that can be removed from the defibrillator system and that are easy to insert and remove.

A simple, safe handling and easy operation are achieved if the capacitor units are contained in respective receiving modules and by them, can be interchangeably coupled to or decoupled from the defibrillator.

For example in a "classic" defibrillator used in an emergency situation (emergency medical services, treatment by an emergency physician), a simple, clear assignment of a receiving module as a function of a particular patient is assured because the defibrillator has a measuring device for detecting the patient impedance and a data output is provided, that can be used to assign a capacitor unit, which is matched to the impedance, to the defibrillator. In this case, the information can be output acoustically and/or optically and relates directly or indirectly to the receiving module to be coupled.

Other advantageous steps for a clear assignment of a suitable capacitor unit as a function of the impedance of a patient to be treated include providing the different receiving modules with different identifying markings clearly associated with the respective capacitance. For example, the receiving modules of a particular capacitance can all be identified with a red marking or another clear, quick-to-read indication, while all receiving modules with another capacitance for a different patient impedance can be provided, for example, with a green indicator or with some other clear indication. The limits of the impedance ranges to which respective capacitor units are assigned can be determined and also at a later time, other impedance ranges and other capacitor units assigned to them can be selected and prepared if this appears suitable and corresponding knowledge is available. At least two, but preferably three or four capacitor units of different capacitances should be available.

The defibrillator can be in the form of a device to be permanently worn by a patient and the measuring device is embodied for continuously monitoring the patient impedance and has an evaluation device and the evaluation device is to issue a warning signal if a predetermined critical limit is exceeded or undershot due to a change in the patient impedance.

One advantageous matching and assignment is achieved if the capacitance of the capacitor unit is established as a function of at least one parameter value of the defibrillation pulse to be administered to the patient.

In other embodiments, the at least one parameter value of the defibrillation pulse relates to the energy, the amplitude ratio of the current at the beginning and end of a pulse phase, or the amperage at the beginning of a pulse phase, or a combination of at least two of these values.

The steps contribute to a safer operation and reliable function because to safeguard the capacitor unit, in particular in the event that a residual voltage is present, an automatically acting covering mechanism automatically unlocks when the receiving module is coupled into position and automatically locks upon removal of the receiving module.

The covering mechanism can have a discharging resistor by which a controlled discharge of the capacitor unit occurs with an approaching removal of the receiving module.

These steps avoid an inadvertent short-circuiting of the capacitor if a residual voltage is present.

The invention is based on the following considerations and knowledge. Normally, defibrillators have a capacitor arrangement of a fixed size with a capacitance selected so that over the greatest possible range of patient impedances in combination with adapted high voltages, currents in a physiologically effective form (as regards amplitude and chronological progression) are transmitted through the body. A pulse form in widespread use is the so-called biphasic truncated exponential (BTE) pulse in which the capacitor that is charged to a high voltage is biphasically discharged via the patient resistance through the use of a corresponding control.

This involves the following problems.

High peak currents occur at a low patient impedance, with the risk of tissue damage.

Low patient currents occur at high impedance, which can jeopardize the defibrillation results.

A powerful drop in current (low ratio of current amplitudes at the end and the beginning of the shock phase) can occur at low impedances, which can jeopardize the defibrillation results.

These disadvantages are avoided by the steps taken according to this invention.

For a permanently worn monitoring system equipped with an integrated defibrillation unit, the patient-specific impedance is known in advance or is detected by a measuring device. Fluctuations in patient impedance can also occur due to physical effort, circadian variation, etc., but not in the entire bandwidth. According to this invention, a capacitor receiving module that is standardized in its (geometric) size is created for a defibrillation system. This capacitor receiving module includes a capacitor set (capacitor unit) with a capacitance that is matched to the individual patient. The graduation of the covered patient impedances can be designed coarser or finer.

BRIEF DESCRIPTION OF THE DRAWINGS

This invention is explained in greater detail in view of embodiments and in conjunction with the drawings, wherein:

FIG. 1b is a schematic view of a defibrillator equipped with a capacitor unit contained in a capacitor receiving module according to FIG. 1a;

DETAILED DESCRIPTION OF THE INVENTION

Figure 1A:
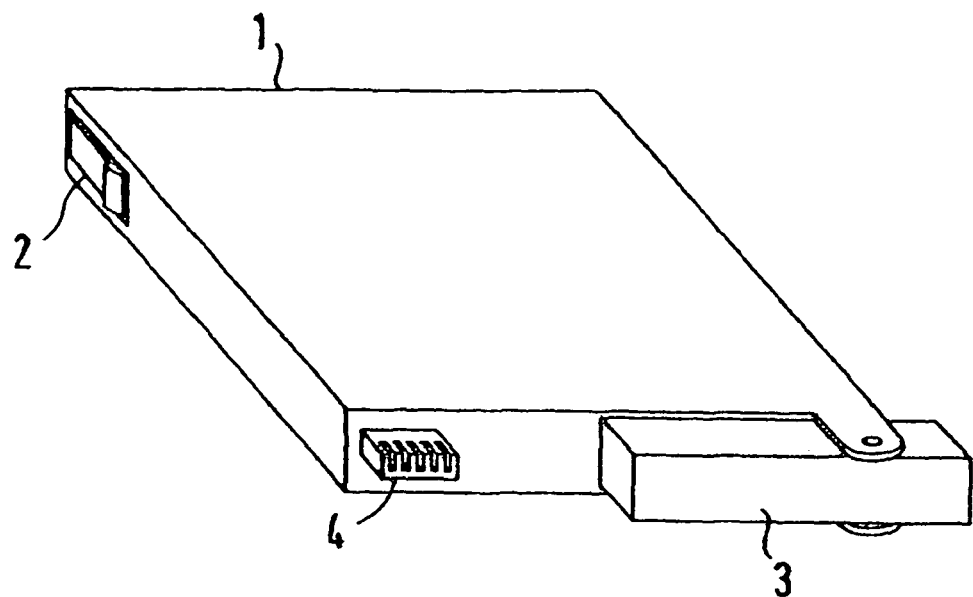
FIG. 1a is a schematic perspective view of a capacitor receiving module.
Figure 1B:
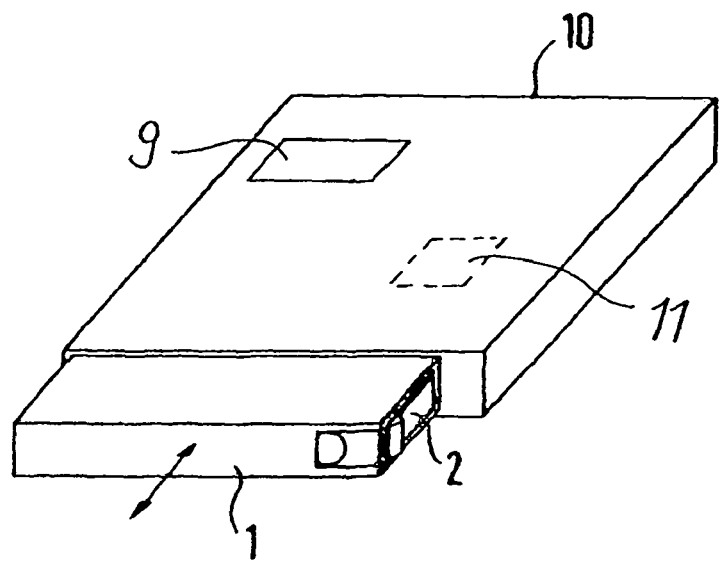

FIGS. 1a and 1b show an example for the embodiment of a capacitor receiving module 1. The capacitor receiving module can be slid into the defibrillation system and locked, as shown in FIG. 1b. The module can be removed again by an unlocking on the bottom side.

Figure 2:
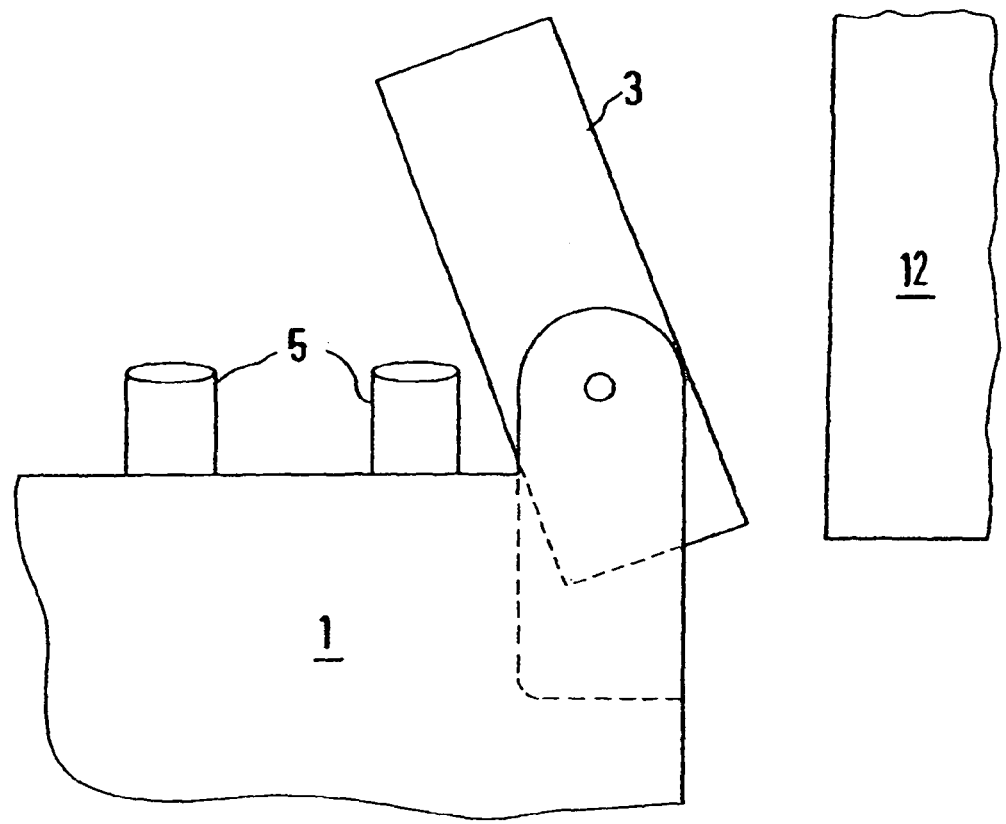
FIG. 2 shows a detail of a capacitor receiving module according to FIG. 1a, with uncovered connection contacts and before insertion into an insertion shaft in a defibrillator housing.
Figure 3:
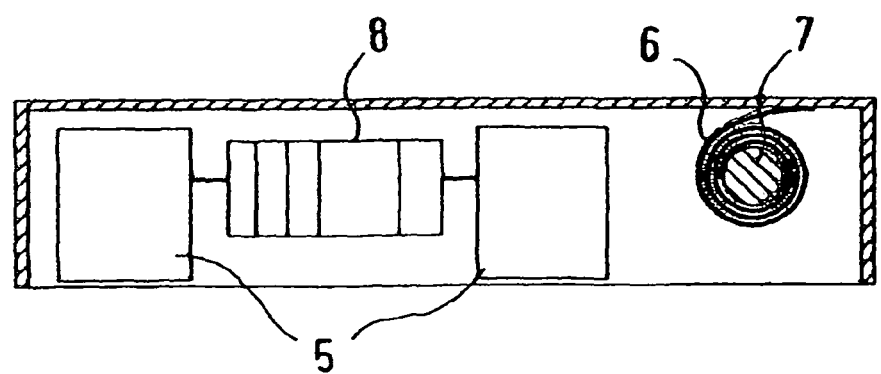
FIG. 3 is a sectional view of a protective cover as shown in FIG. 2, with components contained therein.

FIGS. 2 and 3 show a possible exemplary embodiment of a protecting mechanism. To safely reduce possibly existing residual voltage, the capacitor receiving module 1 includes a mechanism with a device that provides for a safe discharge via a load resistor (discharging resistor 8, see FIG. 3) when the capacitor module is removed from the defibrillator system. As shown in FIG. 2, this mechanism has a protective cover 3 with the integrated discharging resistor 8. The protective cover 3 automatically pivots mechanically around a hinge 7 into an open position when the capacitor receiving module 1 is slid into the defibrillation system 10, thus uncovering the underlying connecting contacts 5 of the capacitor arrangement. Upon removal of the receiving module 1 from the defibrillation system, spring force such as from spring 6 causes the protective cover 3 to snap around the hinge 7 into its closed position. Other embodiment forms of receiving modules are also possible, for example a design that is merely plugged or pivoted into position.

Figure 4A:
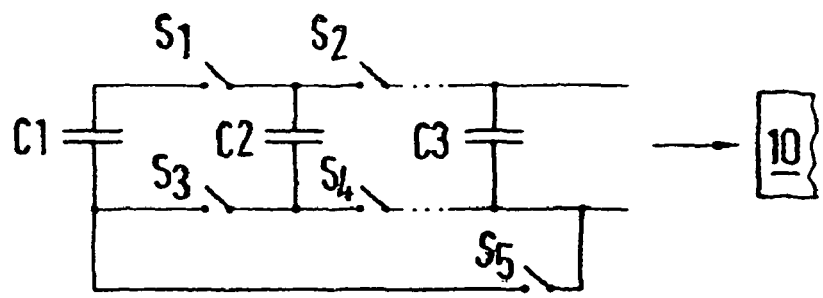
FIGS. 4a, 4b, and 4c show a capacitor arrangement of the capacitor unit before charging, during a charging to a high voltage in a parallel circuit, and during discharging.
Figure 4B:
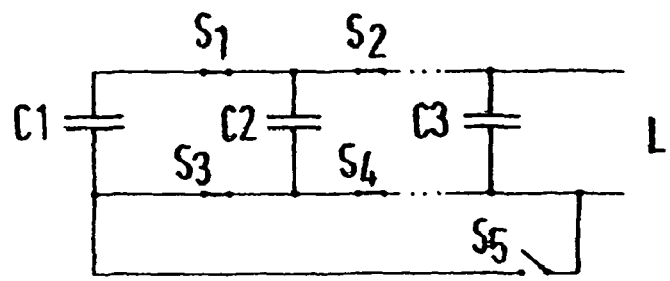
Figure 4C:
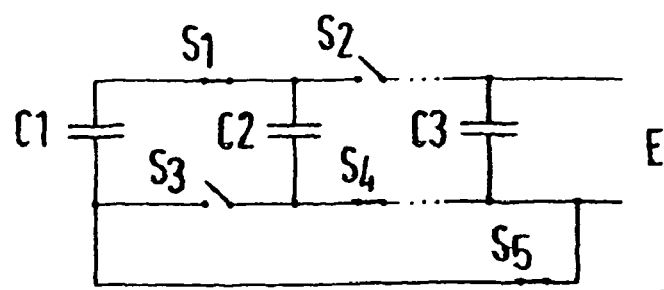

As shown in FIG. 4, the insertion module 1 can have additional active elements S1, S2, S3, S4, S5, which, by a control unit and additional control lines, permit a parallel connection of a plurality of capacitors C1, C2, C3 in the module 1 during the charging L (middle depiction) and permit them to be connected in series for the discharging E (lower depiction).

With the above-mentioned steps, a defibrillator system 10 is achieved, which is individually matched to a patient and is intended for long-term use, in which the energy required for the defibrillation is stored in a capacitor arrangement C1, C2, C3 whose capacitance is matched to the respective patient impedance. The defibrillation system 10 can comprise a plurality of submodules.

The capacitance is advantageously determined by the following pulse form parameters. Energy and amplitude ratio of the current at the beginning and end of a pulse phase can be used. In addition or alternatively, the capacitance is determined by the following pulse form parameters: amperage at the beginning of a pulse phase and amplitude ratio of the current at the beginning and end of a pulse phase.

The capacitor arrangement with the patient-adapted capacitance is accommodated as a unit in a standardized module that can be slid into the defibrillation system 10 or one of its submodules.

The insertion module 1 includes at least one capacitor C1, C2, C3 and a device, which, upon removal of the insertion module 1 from the defibrillation system, assures that possibly existing residual voltage is reduced to zero by the load resistor, specifically the discharging resistor 8, integrated into the insertion module 1. Separate control lines assure that a plurality of capacitors C1, C2, C3 integrated into the insertion module 1 can be connected in parallel and in series.

As FIG. 1b shows, the defibrillator advantageously has a measuring device 11 for measuring a patient impedance and a display device 9 that provides an acoustical or optical display relating to the patient impedance so that an operator is provided information about which capacitor unit or which capacitor receiving module 1 is best suited for treating the patient with the defibrillator. Thus, for example with a "classic" defibrillator in an emergency situation, the emergency medical technician or emergency physician is quickly provided with an indication as to which receiving module 1 should be used to treat the specific patient. The display and a name of the receiving module 1 are matched to each other, such as a "red module," "green module," and the like, so that the use of the capacitor receiving module in the defibrillator housing is particularly simple.

In a defibrillator that is permanently worn by a patient, the measuring device 11 can also have an evaluation device that constantly monitors the patient impedance and also determines if this succeeds or undershoots a predetermined critical limit and if a change would be advisable. In another embodiment, the display unit 9 gives the user or patient a warning signal that an adaptation is required and instructs him or her to change the receiving module.

The invention claimed is:

1. A defibrillator for an external administration to a patient, comprising an energy storage unit for emitting a defibrillation shock and having a capacitor unit with at least one capacitor (C1, C2, C3), the defibrillator further comprising:
   a plurality of capacitor units with capacitances matched to various patient impedances adapted to be interchangeably coupled to the defibrillator;
   a plurality of receiving modules (1), wherein each of the capacitor units are contained in a respective one of the plurality of receiving modules (1) and adapted to be interchangeably coupled to the defibrillator;

wherein the defibrillator has a measuring device (11) for detecting a patient impedance and a data output (9) is assigned to one of the capacitor unit, which is matched to the impedance; and wherein the defibrillator is formed as a device to be permanently worn by a patient and the measuring device continuously monitors the patient impedance and has an evaluation device and the evaluation device issues a warning signal if a predetermined limit is exceeded or undershot with an occurrence of a change in the patient impedance.

2. The defibrillator as recited in claim 1, wherein information can be output acoustically and/or optically and the information relates to the receiving module (1) to be coupled.

3. The defibrillator as recited in claim 2, wherein different receiving modules (1) have different identifying markings clearly associated with the respective capacitance.

4. The defibrillator as recited in claim 3, wherein a capacitance of the capacitor unit is established as a function of at least one parameter value of the defibrillation pulse administered to the patient.

5. The defibrillator as recited in claim 4, wherein the at least one parameter value of the defibrillation pulse relates to an energy, the amplitude ratio of the current at a beginning and an end of a pulse phase, or the amperage at the beginning of a pulse phase, or a combination of at least two of these values.

6. The defibrillator as recited in claim 5, wherein in order to safeguard the capacitor unit if a residual voltage is present, an automatically acting covering mechanism automatically unlocks when the receiving module (1) is coupled into position and automatically locks upon removal of the receiving module (1).

7. The defibrillator as recited in claim 6, wherein the covering mechanism has a discharging resistor (8) by which a controlled discharge of the capacitor unit (C1, C2, C3) occurs with an approaching removal of the receiving module (1).

8. The defibrillator as recited in claim 1, wherein different receiving modules (1) have different identifying markings clearly associated with the respective capacitance.

9. The defibrillator as recited in claim 1, wherein a capacitance of the capacitor unit is established as a function of at least one parameter value of the defibrillation pulse administered to the patient.

10. The defibrillator as recited in claim 9, wherein the at least one parameter value of the defibrillation pulse relates to an energy, the amplitude ratio of the current at a beginning and an end of a pulse phase, or the amperage at the beginning of a pulse phase, or a combination of at least two of these values.

11. A defibrillator for an external administration to a patient, comprising an energy storage unit for emitting a defibrillation shock and having a capacitor unit with at least one capacitor (C1, C2, C3), the defibrillator further comprising:

a plurality of capacitor units with capacitances matched to various patient impedances which adapted to be interchangeably coupled to the defibrillator and, an automatically acting covering mechanism, wherein in order to safeguard the capacitor unit if a residual voltage is present, the automatically acting covering mechanism is adapted to automatically unlock when a receiving module (1) containing the capacitor unit is coupled into position and automatically lock upon removal of the receiving module (1).

12. The defibrillator as recited in claim 11, wherein the capacitor units are contained in respective receiving modules (1) and are or can be interchangeably coupled to the defibrillator.

13. The defibrillator as recited in claim 12, wherein the defibrillator has a measuring device (11) for detecting a patient impedance and a data output (9) is assigned to a capacitor unit, which is matched to the impedance.

14. The defibrillator as recited in claim 11, wherein the defibrillator is formed as a device to be permanently worn by a patient and the measuring device continuously monitors the patient impedance and has an evaluation device and the evaluation device issues a warning signal if a predetermined limit is exceeded or undershot with an occurrence of a change in the patient impedance.

15. The defibrillator as recited in claim 11, wherein the defibrillator has a measuring device (11) for detecting a patient impedance and a data output (9) is assigned to a capacitor unit, which is matched to the impedance.

16. The defibrillator as recited in claim 15, wherein information can be output acoustically and/or optically and the information relates to the receiving module (1) to be coupled.

17. The defibrillator as recited in claim 11, wherein the defibrillator is formed as a device to be permanently worn by a patient and the measuring device continuously monitors the patient impedance and has an evaluation device and the evaluation device issues a warning signal if a predetermined limit is exceeded or undershot with an occurrence of a change in the patient impedance.

18. The defibrillator as recited in claim 11, wherein the covering mechanism has a discharging resistor (8) by which a controlled discharge of the capacitor unit (C1, C2, C3) occurs with an approaching removal of the receiving module (1).

* * * * *